United States Patent
Freeman

(10) Patent No.: US 6,324,698 B1
(45) Date of Patent: Dec. 4, 2001

(54) SPLIT SOCK

(76) Inventor: Carol A. Freeman, 16000 Pemberville Rd., Pemberville, OH (US) 43450

(*) Notice: Subject to any disclaimer, the term of this patent is extended or adjusted under 35 U.S.C. 154(b) by 0 days.

(21) Appl. No.: 09/478,110

(22) Filed: Jan. 4, 2000

Related U.S. Application Data

(60) Provisional application No. 60/115,205, filed on Nov. 7, 1999.

(51) Int. Cl.[7] .................................................. A43B 17/00
(52) U.S. Cl. .............................................................. 2/239
(58) Field of Search .................................. 2/239, 61, 22; D2/980; 66/178 R, 178 A, 185; 602/62, 65, 66, 63

(56) References Cited

U.S. PATENT DOCUMENTS

| | | | |
|---|---|---|---|
| D. 80,129 | * 12/1929 | Le Veque | D2/980 |
| 335,704 | * 2/1886 | Hoult | 66/178 A |
| 1,564,874 | * 12/1925 | Madden | 602/62 |
| 1,724,784 | * 8/1929 | Teichmann | 66/185 |
| 2,344,773 | * 3/1944 | Herbert | 66/185 |
| 3,015,942 | * 1/1962 | Getaz | 66/186 |
| 3,102,271 | * 9/1963 | Wilkerson | 2/239 |
| 3,274,709 | * 9/1966 | Lipinski | 36/10 |
| 3,299,540 | * 1/1967 | Scholl | 36/8.1 |
| 3,975,929 | * 8/1976 | Fregeolle | 66/172 E |
| 4,180,065 | * 12/1979 | Bowen | 128/165 |
| 4,240,160 | * 12/1980 | Imboden et al. | 2/239 |
| 4,571,960 | * 2/1986 | Hursh et al. | 66/196 |
| 5,412,957 | * 5/1995 | Bradberry et al. | 66/178 |
| 5,575,013 | * 11/1996 | Krack | 2/239 |
| 5,617,745 | * 4/1997 | Della Corte et al. | 66/178 |
| 5,724,836 | * 3/1998 | Green | 66/185 |
| 5,867,838 | * 2/1999 | Corry | 2/239 |
| 6,044,497 | * 4/2000 | Richardson | 2/239 |
| 6,047,571 | * 4/2000 | Juniman | 66/178 |

* cited by examiner

Primary Examiner—John J. Calvert
Assistant Examiner—Alissa L. Hoey
(74) Attorney, Agent, or Firm—John C. Purdue; David C. Purdue

(57) ABSTRACT

An improved sock or slipper sock comprising a toe portion for covering the toes of a foot, a continuous calf portion for surrounding a calf, and a slit, slot or opening located between the toe portion and the calf portion is disclosed. The slot terminates, at one end, adjacent to the toe portion and terminates at the other end, adjacent to the calf portion. In a preferred embodiment, the slit is buttonhole stitched for durability. When the sock is first put on a foot, the calf portion is held open and gently slid over the toes, the foot and up the calf where it is released and gently grips the calf. The toe portion is then manipulated to cover the toes of the foot. The slit opens, as necessary, to accommodate any dressing that might be anywhere on the foot. When the dressing needs to be changed, the calf portion remains in its position around the calf, or is adjusted downwardly somewhat, and the toe portion of the sock is removed from toes, leaving the sock attached to the person, about his or her calf. The sock is then manipulated to expose the old dressing, through the slot, the dressing is changed and the toe portion is repositioned over the toes.

8 Claims, 2 Drawing Sheets

SPLIT SOCK

This application claims benefit of Provisional Application Ser. No. 60/115205 filed Nov. 7, 1999.

BACKGROUND OF THE INVENTION

1. Field of the Invention

The present invention relates generally to socks, slipper socks and the like and especially to such socks which are split on an upper portion between a toe portion and a calf portion.

2. Description of the Prior Art

Socks and slipper socks are well known garments. A person whose foot is wounded or injured knows that conventional socks and slipper socks can aggravate a foot wound or injury when they are pulled onto or off of a foot. In the case where a foot wound is bandaged, the bandage must be changed with regularity and conventional socks and slipper socks, if worn, must be pulled off of and onto the foot, often traumatizing the wound and delaying the healing process. The same problem arises in the case of a foot with a surgical incision which is bandaged.

Wound care has received a lot of attention in recent years. Some wounds are chronic under normal conditions and extreme care is required to effect healing. Feet are susceptible to decubitis ulcers which can be extremely difficult to heal, especially in persons who have poor or restricted circulation such as diabetics. Diabetic ulcers frequently appear on a patient's toes which are especially vulnerable to cold. Foot coverings are essential in such cases to keep the persons feet warm, clean and dry. People with diabetic ulcers on their feet wear what is called an orthowedge shoe which allows a person's weight to rest on the heel of the foot, reducing or eliminating pressure on the toes. The Velcro® top of an orthowedge goes over the foot and must be accommodated by any foot covering. Decubitis ulcers are often treated with a topical medication and dressed to promote healing. Frequent dressing changes, such as twice daily, are often indicated but the action of pulling a sock on and off of a foot to change a dressing can disturb the dressing and the wound, delaying the healing process by exacerbating the wound.

U.S. Pat. No. 5,575,013 ("Kräck"), the disclosure of which is incorporated herein by reference, discloses an "easy on sock" which is split from a toe portion all the way through an upper portion of the sock so that it may be wrapped around, rather than pulled onto, a foot. A plurality of hook and loop closure strips are provided to close the split and secure the sock around a foot. Although this construction addresses the problem of minimizing trauma to a foot during application and removal of the sock, there is a better way.

SUMMARY OF THE INVENTION

The present invention is based upon the discovery of an improved sock or slipper sock comprising a toe portion for covering the toes of a foot, a continuous calf portion for surrounding a calf, and a slit or slot located between the toe portion and the calf portion. The slit terminates, at one end, adjacent to the toe portion and terminates, at the other end, adjacent to the calf portion. In a preferred embodiment, the slit is buttonhole stitched for durability. When the sock is first put on a foot, the calf portion is held open and gently slid over the toes, the foot and up the calf where it is released and gently grips the calf. The toe portion is then manipulated to cover the toes of the foot. The slit opens, as necessary, to accommodate any dressing that might be on the foot anywhere. When the dressing needs to be changed, the calf portion remains in its position around the calf, or is adjusted downwardly somewhat, and the toe portion of the sock is removed from toes, leaving the sock attached to the person, about his or her calf. The sock is then manipulated to expose the old dressing, through the slot, the dressing is changed and the toe portion is repositioned over the toes. The sock accommodates an orthowedge appliance and makes dressing changes, even on toes, easier. Moreover, the sock provides all important protection to feet from cold and this is so important for diabetics who usually experience a loss of feeling in extremities like feet which are, therefore, extremely susceptible to injury and cold.

Accordingly, it is an object of the present invention to provide a sock which covers a person's toes, most of a person's foot and a portion of a person's calf, and is provided with a slit which terminates at one end adjacent to the toe portion and terminates at the other end adjacent to the calf portion.

It is a further object of the invention to provide such a sock which can be partially removed to facilitate dressing changes or other foot care procedures without causing damage to a wound or injury on the foot.

It is yet a further object of the invention to provide a sock which will accommodate an orthowedge appliance It is still a further object of this invention to provide a method for protecting a foot with a sock, partially removing the sock to treat the foot and replacing the sock on the foot without aggravating any wound or injury on the foot or toes.

It is a primary object of this invention to provide an improved sock or slipper sock.

These any other objects and advantages of the present invention will no doubt become apparent to those skilled in the art after having read this detailed description of the invention including the following description of the preferred embodiment which is illustrated by the various figures of the drawing.

DETAILED DESCRIPTION OF THE PREFERRED EMBODIMENTS

Figure 1:
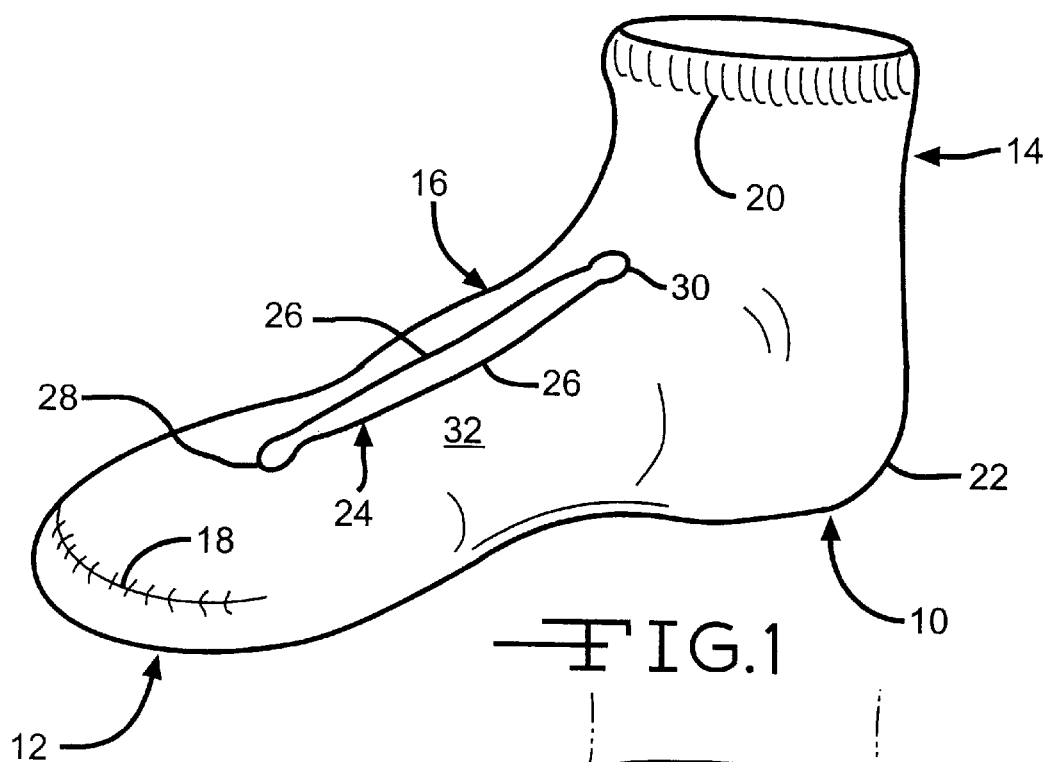
FIG. 1 is a perspective view of a sock according to the present invention.

Referring to FIG. 1, a sock according to the present invention is indicated generally at 10. The sock 10 comprises a toe portion 12, a calf portion 14 and a central portion 16 between the toe portion 12 and the calf portion 14. The toe portion is stitched closed, as indicated at 18 although a toe portion formed by another means is certainly contemplated within the scope of the invention which includes a generally closed toe portion 12. The calf portion 14 is open at the top but is continuous in the sense that it will encircle a wearer's calf completely. The calf portion 14 may include elastic securance means indicated at 20 for gripping the calf of a wearer.

The central portion 16 of the sock extends from the toe portion 12 to the closed calf portion 16 and includes a heel portion 22. It will be appreciated that the sock 10 may be in the nature of a "tube" sock which does not have a distinct heel portion until it is put on a foot. By conforming to a foot, a heel portion of a tube sock takes shape, and this is certainly within the scope of the present invention as is a sock having a sewn heel portion (not illustrated) or a heel portion formed by other means.

Within the central portion 16, a slot or opening, indicated at 24, is defined by side edges 26. The slot 24 is further defined by a toe end portion 28 and a calf end portion 30. The slot 24 is centrally located, in the embodiment illustrated in FIG. 1, in an upper surface 32 of the central portion 16. It will be appreciated that the opening can be offset, if desired, from the central of the upper surface 32 of the central portion 16, within the scope of the present invention. If desired, the side edges 26, the toe end portion 28 and the calf end portion 30 can be reinforced by stitching, similar to the way that a button hole is reinforced by stitching. The length of the slot 24, as discussed below in more detail, can vary although a preferred length is about six to eight inches. At a minimum, the slot 24 must be long enough that, when opened, its edges define an opening larger than the circumference of a foot for which the sock is sized. Moreover, the slot 24 does and must terminate short of the toe portion 12 and the calf portion 14 so that these portions remain closed at all times.

Figure 2:
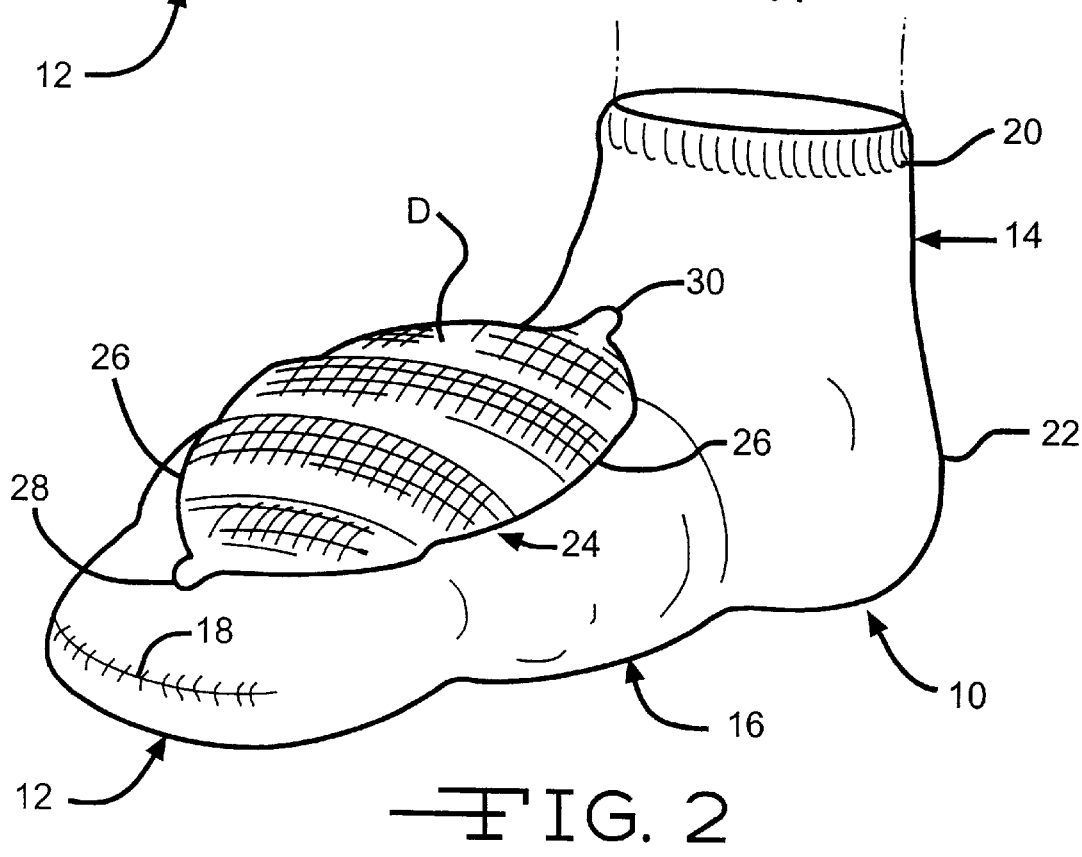
FIG. 2 is a perspective view of a sock according to the invention applied to a foot with a dressing on it.

Referring now to FIG. 2, the sock 10 is illustrated as it would appear on a foot (not shown) having a large dressing D on a wound (also not shown) on an upper portion of the foot. The side edges 26 of the slot 24 have spread, as necessary, to accommodate the dressing D while minimizing pressure on the dressing D and the wound it covers. The toe portion 12 and the calf portion 14 hold the sock 10 securely in place.

Figure 3:
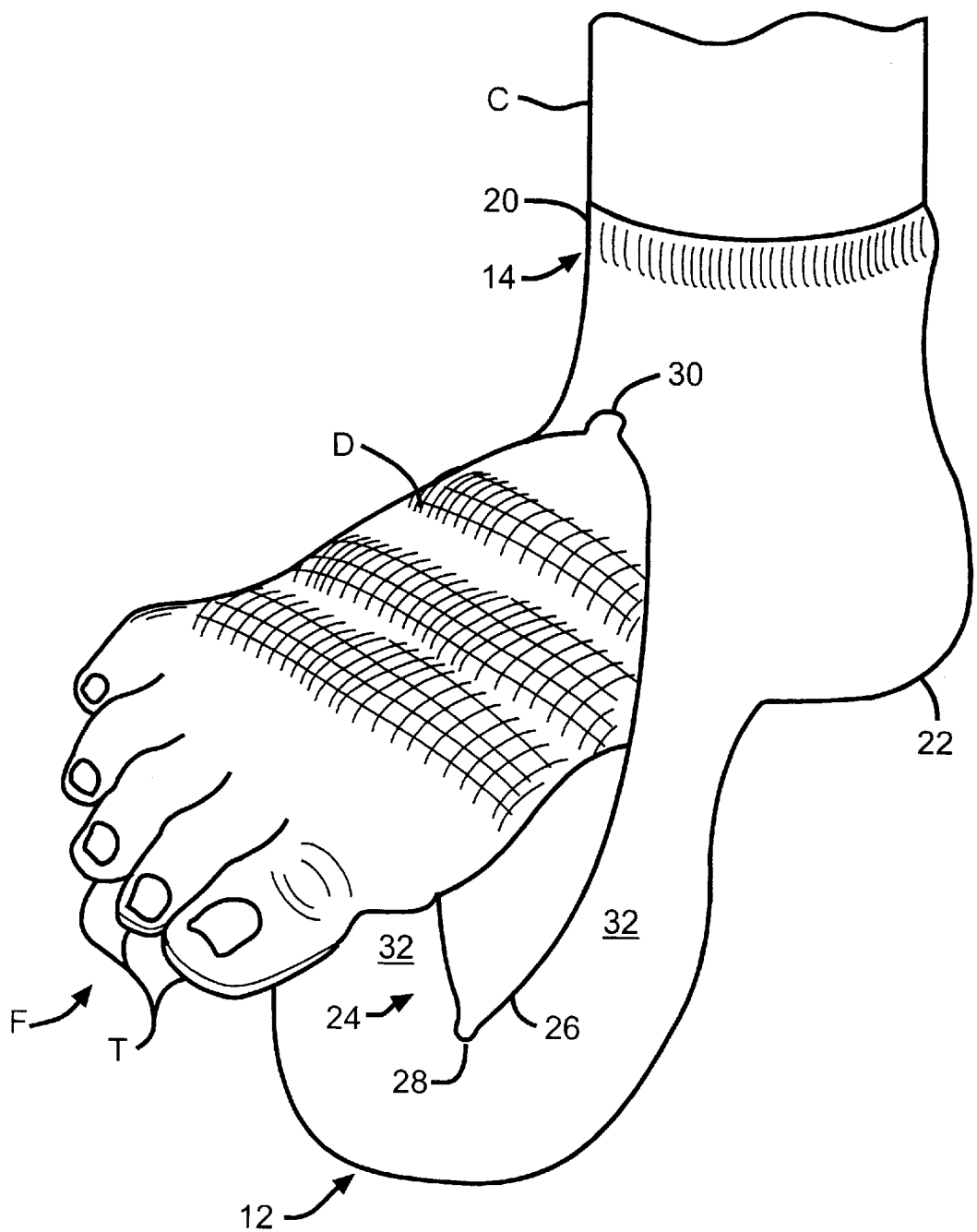
FIG. 3 is a perspective view, similar to FIG. 2, showing the sock partially removed from the foot so that the dressing can be changed.

Referring now to FIG. 3, the sock is illustrated in an intermediate stage in a method, according to the invention, for changing a dressing D on a foot F. The calf portion 14 remains in place around a calf C of a wearer. The toe portion 12 has been removed from toes T of the foot F and the toes T and a lower portion of the foot have been exposed as by spreading the side edges 26 and pulling the toe portion 12 and the central portion 16 back towards the heel portion 22. As a consequence, the dressing D is completely exposed yet the sock 10 remains secured to the wearer by the calf portion 14, all without disturbing the dressing D or the wound it covers. Similarly, a dressing (not shown) on a toe wound could be exposed for changing or care without disturbing the dressing. If desired, the toe portion and the central portion 16 can be further pulled back to expose the heel (not shown) of the wearer in order to change a dressing there. Once the dressing D has been changed, the toe portion 12 is repositioned as shown in FIG. 2 so that it covers the wearer's toes.

FIG. 3 also illustrates an intermediate stage in a method for initially putting the sock 10 on a foot. The first step is to grasp the calf portion 14 adjacent the open top and to open it wide so that the continuous calf portion can be slid around and over a foot up to a wearer's calf C. A wearer's toes and foot are guided though the slot 24 which is also preferably opened wide. The toe portion is then guided onto and over a wearer's toes until the sock is positioned on a foot, substantially as shown in FIG. 2. Any slack in the central portion 16 of the sock can be taken up by sliding the calf portion 14 up the wearer's calf. At all times, contact between the sock 10 and the dressing D is entirely minimized. Further, the sock facilitates the changing of a dressing with only partial removal of the sock required, further minimizing trauma to a wound or injury on a foot or toe.

The foregoing description is intended to enable one skilled in the art to practice this invention and constitutes the best mode presently known to the inventor for carrying out the invention. Modifications and adaptations of the invention, as described herein, will undoubtedly occur to those skilled in the art and, although not described herein, may nevertheless fall within the spirit and scope of the invention as defined in the claims.

I claim:
1. A sock for a foot having a given circumference, the sock comprising
   a toe portion for covering the toes of the foot,
   a calf portion comprising a continuous band of material which, in use, encircles a portion of a wearer's calf, and
   a central portion connected to said toe portion and to said calf portion, said central portion comprising
      a plurality of edges which define an opening,
      a toe end portion associated with the opening, said toe end portion being positioned adjacent to and short of said toe portion, and
      a calf end portion associated with the opening.
2. The sock claimed in claim 1 wherein the opening defined by said edges, said toe end portion and said calf end portion is bigger than the circumference of the given foot.
3. The sock claimed in claim 2 wherein said calf portion is elasticized.
4. The sock claimed in claim 1 wherein the opening in said central portion is defined in an upper surface of said central portion.
5. The sock claimed in claim 1 wherein said calf portion is elasticized.
6. A method for applying a sock to a foot and calf, said sock comprising
   a toe portion for covering the toes of the foot,
   a calf portion comprising a continuous band of material which, in use, encircles a portion of a wearer's calf, and
   a central portion connected to said toe portion and to said calf portion, said central portion comprising
      a plurality of edges which define an opening,
      a toe end portion associated with the opening, said toe end portion being positioned adjacent to said toe portion, and
      a calf end portion associated with the opening,
said method comprising the steps of opening said calf portion and sliding it over the foot and up the calf so that a portion of the foot is outside the opening, and positioning said toe portion over the toes of the foot and covering at least a portion of the foot with said central portion.
7. The method claimed in claim 6 wherein, after the toes of the foot are covered by the toe portion, the calf portion is adjusted so that the toe portion is held snugly on the toes.
8. A method for changing a dressing on a foot covered by a sock, said sock comprising
   a toe portion for covering the toes of the foot,
   a calf portion comprising a continuous band of material which, in use, encircles a portion of a wearer's calf, and
   a central portion connected to and said toe portion and to said calf portion, said central portion comprising
      a plurality of edges which define an opening,
      a toe end portion associated with the opening, said toe end portion being positioned adjacent to and short of said toe portion, and
      a calf end portion associated with the opening,
said method comprising the steps of removing said toe end portion from the toes of the foot and manipulating the toes through the opening in said central portion, manipulating the sock and foot to expose the dressing through the opening in said central portion, changing the dressing, and manipulating the foot and sock to recover the foot with said central portion and to recover the toes of the foot with said toe end portion.

* * * * *